United States Patent

Reznick

[11] Patent Number: 5,947,119
[45] Date of Patent: Sep. 7, 1999

[54] THERAPEUTIC PROCESS AND APPARATUS FOR NASAL PASSAGES

[76] Inventor: Jerald M. Reznick, 2208 Washington Ave., Santa Monica, Calif. 90403-2132

[21] Appl. No.: 08/962,073

[22] Filed: Oct. 31, 1997

[51] Int. Cl.$^6$ .................................................. A61M 15/08
[52] U.S. Cl. ............................. 128/204.12; 128/206.11; 128/207.18
[58] Field of Search ....................... 128/201.18, 203.18, 128/203.22, 206.11, 207.18, 204.12, 206.18, 206.25, 207.13

[56] References Cited

U.S. PATENT DOCUMENTS

| | | |
|---|---|---|
| 480,505 | 8/1892 | Midgley et al. |
| 682,123 | 9/1901 | Wilson . |
| 1,579,486 | 4/1926 | Pletcher ............................. 128/206.11 |
| 1,819,884 | 8/1931 | Fores .................................. 128/206.11 |
| 2,151,227 | 3/1939 | Pawelek . |
| 2,335,936 | 12/1943 | Hanlon ............................... 128/207.18 |
| 2,340,223 | 1/1944 | Krill ................................... 128/206.11 |
| 2,528,303 | 10/1950 | Gillespie . |
| 2,674,245 | 4/1954 | Tanditter . |
| 2,890,695 | 6/1959 | Safstrom . |
| 3,145,711 | 8/1964 | Beber ................................. 128/206.11 |
| 3,457,917 | 7/1969 | Mercurio . |
| 3,463,149 | 8/1969 | Albu . |
| 3,722,509 | 3/1973 | Nebel ................................. 128/206.11 |
| 3,884,223 | 5/1975 | Keindl . |
| 3,988,033 | 10/1976 | Vacha . |
| 4,052,983 | 10/1977 | Bovender . |
| 4,172,613 | 10/1979 | Furando . |
| 4,220,150 | 9/1980 | King . |
| 4,221,217 | 9/1980 | Amezcua ........................... 128/206.11 |
| 4,280,493 | 7/1981 | Council ............................. 128/207.18 |
| 4,316,300 | 2/1982 | Lewis . |
| 4,573,461 | 3/1986 | Lake . |
| 4,955,945 | 9/1990 | Weick ................................ 128/203.12 |
| 4,973,279 | 11/1990 | Baumann . |
| 5,117,820 | 6/1992 | Robitaille .......................... 128/206.11 |
| 5,392,773 | 2/1995 | Bertrand ............................ 128/206.11 |
| 5,476,091 | 12/1995 | Johnson ............................. 128/200.24 |
| 5,479,944 | 1/1996 | Petruson ................................ 128/858 |
| 5,706,800 | 1/1998 | Cronk et al. ...................... 128/200.24 |
| 5,816,241 | 10/1998 | Cook ................................. 128/200.24 |
| 5,842,469 | 12/1998 | Rapp et al. ....................... 128/200.24 |
| 5,850,834 | 12/1998 | Yoshida et al. ................... 128/204.12 |

*Primary Examiner*—John G. Weiss
*Assistant Examiner*—Joseph F. Weiss, Jr.
*Attorney, Agent, or Firm*—Cislo & Thomas LLP; Daniel M. Cislo, Esq.

[57] ABSTRACT

An air flow control device for the nose has an air flow control element for directing air flow in a selected manner when disposed in a nasal cavity. The flow control element deflects air toward nasal hair for natural filtering, mucous membranes to enhance lubrication, mucous flow, and contaminant capture and processing, or a selected nasal passage, for example, to decrease flow of air to upper regions of the nose and therefore decrease flow to the sinuses. The device also includes an adhesive layer to directly adhere the device to the interior of the nose, or a strip such as a clear adhesive strip to adhere the device to the interior of the nose and the septum. The air flow control element may have any one of numerous shapes such as curved, straight, double-curved, ridged, mesh, oval, rectangular, semicircular, crescent or otherwise. The device may also have louvers positioned to open or close in response to air inspiration or expiration, as selected by the user, and may include chambers or open cell material for storing a medicinal or other substance to disperse within the nose in response to pressure, air flow, liquid flow or otherwise. The device is preferably smaller in cross-section than the cross-section of the user's nasal passages to avoid total blockage in air flow and thus works by regulating or deflecting air to supplement and enhance the natural processes performed by the nose rather than substituting for them and overriding natural processes.

20 Claims, 4 Drawing Sheets

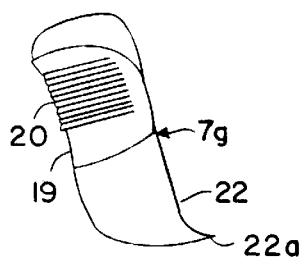
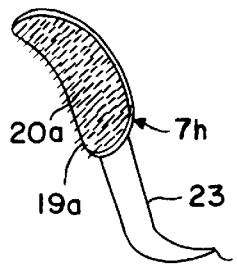
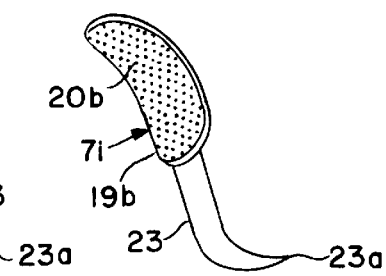
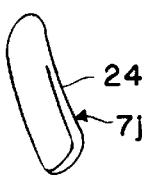
FIG.9  FIG.10  FIG.11  FIG.12
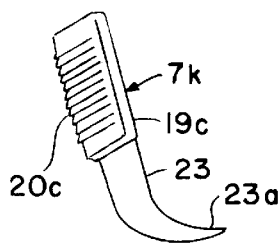
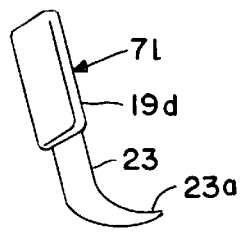
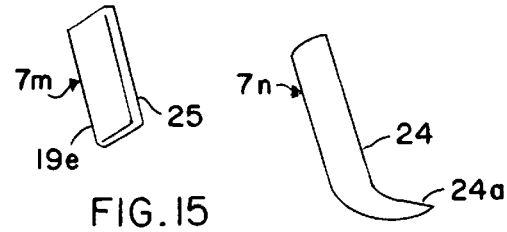
FIG.13  FIG.14  FIG.15  FIG.16
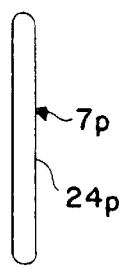
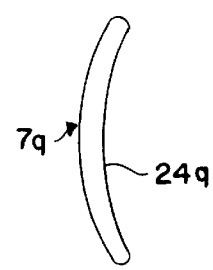
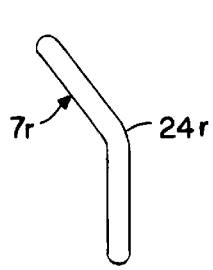
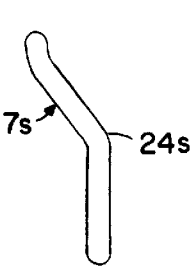
FIG.17  FIG.18  FIG.19  FIG.20
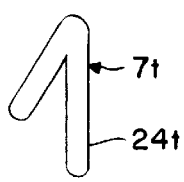
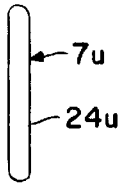
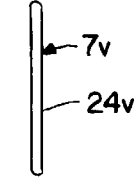
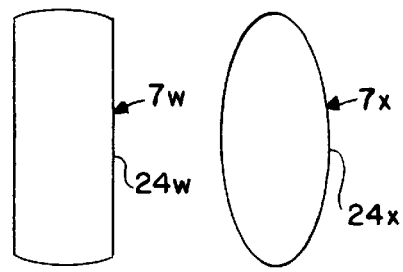
FIG.21  FIG.22  FIG.23  FIG.24  FIG.25

THERAPEUTIC PROCESS AND APPARATUS FOR NASAL PASSAGES

BACKGROUND OF THE INVENTION

1. Field of the Invention

This invention relates to nasal therapeutic devices and in particular to a nasal air flow controller.

2. Description of the Related Art

Many people suffer from discomfort caused by pollen, dust, bacteria, viruses, and other airborne contaminants. The body has natural mechanisms to fight such contaminants. Many such processes are located in the nasal cavity. As this is a known entrance to the body for such contaminants, the issue has been addressed by prior art.

There are numerous patents and devices for nasal devices and filters, some of which hold medicaments and disburse them upon breathing in or by other means. Many nasal devices are in the form of a plug, which is essentially force-fit into the nasal passages or within the entire nasal cavity. These plugs may be made of spongy material, although some are of a more rigid nature. Generally, most filters are supported by a kind of clip which attaches to the septum and holds filters within both nasal cavities. For example, U.S. Pat. No. 4,220,150 to King teaches a nasal dust filter having filter caps with a septum bridge element while U.S. Pat. No. 3,463,149 to Albu teaches filter plugs. U.S. Pat. No. 5,117,820 to Robitaille teaches a nasal filter of a spongy material inserted and wedged into the nostril. U.S. Pat. No. 3,884,223 to Keindl teaches a nasal filter with a one-way valve.

A problem with most of these devices is that they can readily become clogged. Even without becoming clogged, they can block so much air flow that the user must breathe through his or her mouth. This defeats the purpose of the filter or device. Moreover, these filters tend to be uncomfortable due to their size, and also are often aesthetically obtrusive. In addition, these filters generally do not take advantage of the natural functions performed by the nasal passages, and in particular the mucous membranes, hair and multiple air inlet structure. In fact, they tend to prevent and hinder natural processes. What is needed is a nasal device that is physically and aesthetically nonobtrusive, and which controls air yet will not reduce air flow to the point where the user is forced to breathe through the mouth.

SUMMARY OF THE INVENTION

In one embodiment, the invention provides a nasal air flow deflector having an air flow deflection element, and is fixed to a mounting arm. In another embodiment, there is adhesive on the deflection element for directly adhering to the inner wall of the nose. The deflection element may be formed by a material that is bendable yet will retain the shape to which it is bent. Thus, the element may be bent, or it may be formed in any of a variety of shapes to deflect air flow. The mounting arm may be bent around the septum, or the skin which forms the nostril, penetrate the nostril and hold the deflection element at its end disposed within the nostril proximate or against the mucous membranes at the nasal passages. The arm may have adhesive on it, or it may be an adhesive strip. The size of the filter is preferably substantially smaller than the cross-sectional area of the nasal passages or nares, wherever the element is located.

Air is channeled in such a way to take advantage of the natural processes of the nasal passages including mucous secretion, filtering by nasal hair, and multiple air inlet passages.

Several embodiments of the device are disclosed in which the shape and surface texture of the deflection element vary. In addition, a length of the support arm may be adjustable. Wherever adhesive is used, the device may have a plastic or wax film over the adhesive, which film is removable so that the device may be used. In addition, the device may be formed with a small tab so that it can be readily removed by grasping the tab.

The invention influences natural processes by regulating, directing and conditioning nasal air flow, such as by an increase, decrease, abatement, or other effect on operation of the natural nasal processes. This beneficially permits desired processes or functions to be achieved and/or influences prophylactically, responsively and/or in anticipation of conditions.

The human respiratory tract exchanges oxygen and carbon monoxide between atmospheric air and blood. The nose, which also performs olfactory and other sensory functions, is the air processor of the respiratory system. It is responsible for warming, cooling and humidifying inspired air, conserving moisture and heat from expired air, removing and/or combating the effects of particulate matter, and contaminants, and maintenance of airway resistance appropriate for physiological needs. It is responsive to the need for oxygen for cellular respiration and the necessity to react to environmental situations. These requirements are managed by controlling various functions including air flow and circulation patterns, filtration, production of immunoglobulin and interferon bearing mucous, ciliary mucous transport, sensor activated reflexes, and air resistance.

Air passage to the pharynx and the remainder of the respiratory tract is regulated by turbinates, bony formations on the lateral wall of the nasal cavity covered by erectile mucosa that may enlarge or shrink, affecting air resistance, as well as the ability to thermalize, humidify and perform other functions.

The nose has a finite capacity to perform air-processing functions. Regulating air-flow influences those functions. Control of air-flow volume affects the duration of natural process contact thereby influencing performance. Regulating pressure of inspired and expired flow affects particulate repulsion and the rate of disposal of contaminants. Nasal cavity and/or nares expansion decreases air-flow resistance, enhancing pulmonary function in situations of high activity as well as during sleep.

The body's natural mechanisms are not effective on contaminants with which they do not come in contact. Directing air-flow to be in closer and/or repeated contact with or proximity to natural processes increases their functionality.

Natural-process functions, as well as sinus cavities, olfactory sensors and connected or related areas, are located in, and/or accessed through, specific regions within the nasal cavity. Air flow may be directed as to influence their performance or state.

In another embodiment, the device may be a thin-film outer layer formed, cut, textured, scored, embossed, debossed, scribed, perforated, ridged, notched or vary in density or thickness or have a valve mechanism so as to permit the regulated transfer or dispensing or absorption of substances or conditions (temperature, electrical, chemical, magnetic) between layers or between the device and its environment. This includes opening of multiple chambers to establish contact between substances to initiate chemical reactions resulting in new substances and/or the release of energy. In the embodiment, the device has an inner layer which may be absorbent, under pressure, compressed, substance containing, saturated, or forming or holding a substance vessel.

The device incorporates a plurality of planar surfaces or parallel rectilinear planes attached on one or more sides to an encompassing layer at an angle of incidence such that exposure to inspired and expired air-flow is different and/or the position of which may change responsive to air flow or substance or condition. This permits implementation of different functions and/or degree of functionality based on air flow direction.

Multiple segment devices incorporate a plurality of functional device embodiments so as to perform different functions defined geographically or relatively including dispensing substances by capillary action, wicking or otherwise, such as gravity, or may incorporate electrical circuitry, batteries, or capacitors.

The device influences the pressure and/or rate of air flow, and may direct air flow to influence other functions of the device, e.g., by channeling air to a filtering or dispensing area of the nose and/or device.

The device may acquire static charge from air flow or accumulate and spread a mucous coating. The device influences temperature due to thermal retention and radiation, moisture absorption and dispensing, compression, friction, nasal passage volume and/or flow rate.

The device may be of a single material of open-cell structure which is saturated with a substance that is dispensed conditionally. The device is disposed within a user-controlled volume of the nasal passage, and may include portions positioned exterior of the nares.

The device may be composed of a soluble or dissolvable substance containing chambers of different thicknesses enabling regulated dispensing of substances over time.

The device positioning function is achieved by establishing secured contact with the human body by means of pressure, vacuum, suction or biological or dermal adhesive properties present in or on a portion or the entirety of the device, which used entirely internally, or portions of which may circumscribe in whole, or part, the exterior septum or contact other internal and/or external body surfaces.

Positioning functions may be for stable or dynamic results by means of joints, hinges, levers, wheels and axle, pressure and/or tension. Positioning functions may be embodied by a device exhibiting properties of color, size, pliability or rigidity as may be requisite for comfort, personal preference, aesthetic, physiological and/or situational requirements. Positioning functions may be embodied by a device capable of maintaining shape impressed upon it and adhere by allowing user adjusted pressure positioning to the septum or nares.

Positioning functions may be embodied by a device constructed of flexible film, the whole or portions of said film may have adhesive properties or coating and/or be scored, embossed, debossed, scribed, perforated, ridged, notched or vary in density or thickness in periodic lateral lines, patterns or sections so as to allow release of bodily secretions, and permit excess length to be removed easily in segments across the width, without the use of tools.

Positioning functions may be embodied by devices that may be positioned and/or used individually. This permits the use of device implementing complementary or different process functions.

Positioning functions may be embodied by device that may itself exhibit properties and be of form and material allowing the performance of all, certain, complementary, supplemental, or independent of, the process implementing function.

The positioning element may be capable of, bonded to, or integrally constructed with, material(s) which may be permeated, surface treated, or contain microencapsulated substances that may be released to condition or treat the regions both within the nose and exterior to the nares.

The positioning element may be capable of, or have bonded or constructed integral to it, material(s) that may be formed in a manner to affect air-flow exterior to the nares. This may be effective in diverting particulate matter, preventing entry.

In various embodiments, the positioning element may exhibit properties as necessary or desired in a multitude of circumstances and as such may be used for removal of the internal element, have adhesive properties function in packaging and/or disposal, dissolve over a period of time relative to exposure to various environmental conditions of gaseous elements, air, moisture, light, temperature, and pressure, or react specifically or generally to various environmental conditions or the present of certain elements by releasing substances, changing size, form or color.

An example of this would be a multi-layer system consisting of a fibrous or open-cell material bonded and sealed under pressure, along the edges and/or in patterns upon the surface, between two thin-film polymer layers by means of an environmentally sensitive adhesive. Bonds or portions thereof release under prescribed conditions allowing inner section expansion and exposure to the environment thereby facilitating the dispensing of moisture or substances and/or the activation of the inner section properties (absorptive, in this example), such as to mitigate, treat, signal conditions or otherwise react situationally.

The device may be capable of attracting, absorbing particulate, chemical, molecular or organic matter. The device may be embodied by construction with materials and combinations of materials which are capable of resuming its original shape and volume subsequent to having shape impressed upon it.

Device may have structure/forms, within vestibule or nasal cavity, which have adhesive/viscous surfaces to snare particulate and molecular matter. Device uses physical structure, within nasal cavity to retain heat (energy) from expired air flow. Device uses structure within vestibule or nasal cavity to accumulate, create, establish, conduct, transmit or maintain an electrical charge. This is useful in establishing electrical balance with oral cavity, and in attracting minute particles or viruses.

The device may conduct radiant energy, generate sound (whistle), use a structure vestibule or nasal cavity to create, establish, or maintain an electrical charge, and/or dispense substances (anti-septic, viral, etc.) to regions immediately exterior to the nares which cleanse air prior to entering the body.

An internal device that dispenses substances by means of externally applied pressure, useful in nasal cavity.

The device may be embodied by multiple layers including a thin-film layer or layers which encompasses in whole or part one or more inner layers. The thin-film layer may be the outermost layer or be itself encompassed.

BRIEF DESCRIPTION OF THE DRAWINGS

FIGS. 9–36 show various embodiments of nasal devices in accordance with the invention, FIG. 9 showing an air flow control device with a ridged surface fixed to a stem, FIG. 10 showing an air flow control device similar to FIG. 9 but with numerous hair-like protrusions, FIG. 11 showing a device with numerous pits, FIG. 12 showing a device of varying thickness and a slight convex curve, and no stem, FIG. 13 showing a device with a rectangular shape and a ridged surface, FIG. 14 showing a device with a rectangular shape and a flat surface, and a stem, FIG. 15 showing a device of rectangular shape without a stem, FIG. 16 showing a device which is an elongated extension of a stem, FIG. 17 showing a device like that of FIG. 16 but extending straight, FIG. 18 showing a device with a convex face, FIG. 19 showing a device with a concave face, FIG. 20 showing a device which is double-curved, FIG. 21 showing a device which has a V-shape, FIG. 22 showing a device similar to that of FIG. 17 but shorter, FIG. 23 showing a device similar to that of FIG. 22 but thinner, FIG. 24 showing a device which is substantially rectangular, FIG. 25 showing a device which is substantially oval, FIG. 26 showing a device using a porous, open-cell or foam-like deflection element with a stem, the element having an oval shape and the stem passing through the middle, FIG. 27 being similar to FIG. 26 but the device using only one half the oval, FIG. 28 being similar to FIG. 26 but the device having the stem extend all the way through the oval, FIG. 29 being similar to FIG. 28 but the device having three chambers for medicines, FIG. 30 showing a device similar to that of FIG. 29, but having a large central chamber and numerous capillaries, FIG. 31 showing a device similar to that of FIG. 30 but having multiple chambers with capillary passages in the membranes around each chamber, FIG. 32 showing a mesh or textured device having an oval shape, FIG. 33 showing a device with many jagged members or edges, FIG. 34 showing a device with a plurality of louvers, FIG. 35 showing a device having an adhesive layer or substrate which covers an entire surface of the device, while FIG. 36 shows a device similar to that of FIG. 35 but with the adhesive layer covering only part of the device below the head thereof;

DESCRIPTION OF THE PREFERRED EMBODIMENT(S)

Figure 1:
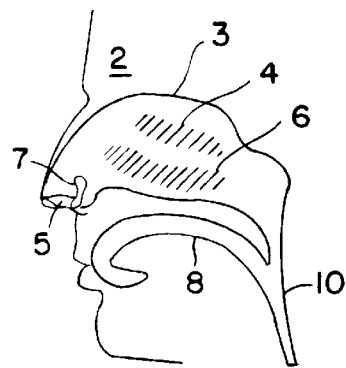
FIG. 1 is a schematic side view of a human head showing one nasal cavity with mucous membranes, the oral cavity and the pharynx and showing a device according to the invention disposed in the nasal cavity.
Figure 2:
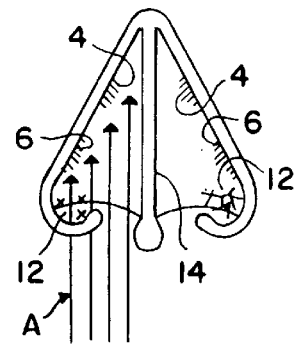
FIG. 2 is a schematic front view of a nose showing normal mucous membranes and air flow into the nose.

FIG. 1 shows a human head 2 having a nasal cavity 3, a nostril 5, upper and lower mucous membranes 4, 6, respectively, a nasal device 7 in accordance with one embodiment of the invention, an oral passage 8, and a pharynx 10 or throat. FIG. 2 shows a slice through the nose of FIG. 1, also showing nasal hair 12, a septum 14, and a diagram of normal air flow represented by arrows A for one of the nostrils. The device 7 in accordance with one embodiment of the invention is constructed and installed in the nasal cavity to control air flow on inspiration and/or expiration from the nose to enhance selected natural functions of the nose. The device 7 is shaped and positioned so that its cross-section will not block the nose, and in fact is substantially less than the cross-sectional area of the opening in the nasal cavity or passages where the device is located, e.g., less than half the sectional area of the cavity in which it is placed.

Figure 3:
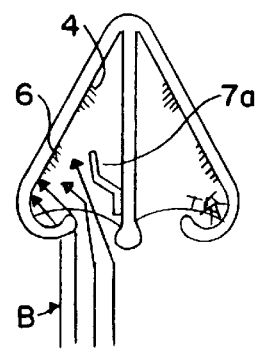
FIGS. 3–7 are views similar to FIG. 2 showing various nasal devices in accordance with the invention and the air flow resulting therefrom, FIG. 3 showing an air flow device for channeling a substantial amount of air flow toward the mucous membranes, FIG. 4 showing a flatter-profiled device for gently channeling air flow toward the membranes, FIG. 5 showing an air flow control device with a concave surface, FIG. 6 showing an air flow device with an oval shape, and FIG. 7 showing an air flow device of FIG. 4 in one nostril and an air flow device of FIG. 3 in the other nostril.
Figure 4:
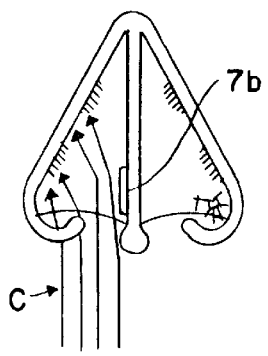
Figure 5:
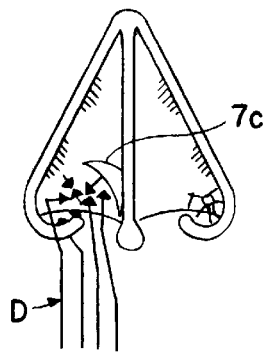

FIGS. 3, 4 and 5 show various devices 7a, 7b, 7c and the air flow represented by arrows B, C and D, respectively, resulting from the devices. The device of FIG. 3 is designed to channel air flow toward the mucous membranes a substantial amount, while the device of FIG. 4 is designed to more gently channel air flow toward the membranes. In fact, the device of FIG. 3 channels more of the air flow towards the lower membrane 6 than the upper membrane 4. The device of FIG. 4 channels air flow more evenly between the membranes. The device of FIG. 5 has a concave surface facing the nostril so that the air flow is made to circulate through nasal hair 12 and in essence create a whirlpool effect so that the hair can perform maximum filtering. In addition, it creates slow flow of air through the nose. This embodiment may be particularly useful where an aroma or medicinal substance is located within the device 7c and dispensed by the device, for example, in response to air flow. The slow flow may be desirable to achieve optimal absorption and distribution of the substance.

Figure 6:
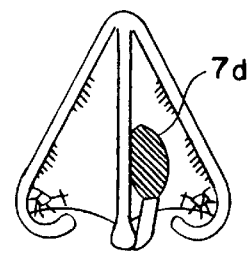
Figure 8:
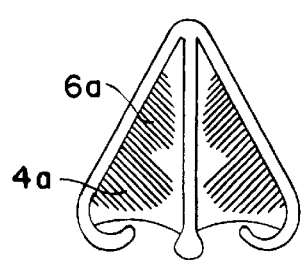
FIG. 8 is a view similar to FIG. 2 showing a state of engorgement of the mucous membranes such as caused by contaminants.
Figure 26:
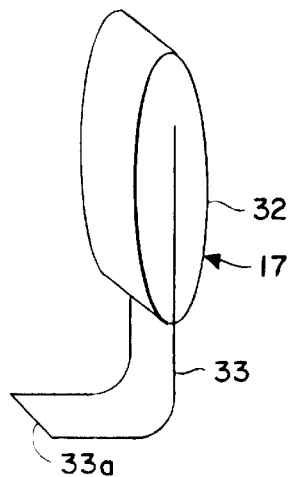

FIG. 6 shows a device 7d having an oval shape and when compared with the view of FIG. 8 showing the inflamed membranes, shows how the device may be used to simulate engorgement of the membranes. Specifically, the device deflects air flow so that it contacts the membranes to enhance the filtering and particulate grabbing function of the membranes.

Figure 7:
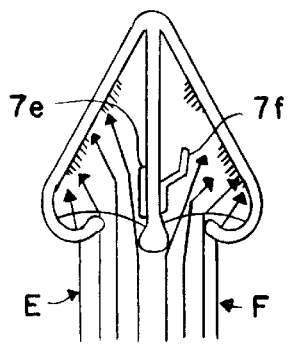

FIG. 7 shows another aspect of the invention in which two different devices 7e, 7f are installed in the left and right nasal cavities and create two different air flow patterns e, f, respectively. In accordance with a feature of one embodiment of the invention, different devices may be installed in each nostril or only one device may be installed in one nostril, to selectively manage air flow in each nostril. For example, the device 7e is like the device 7b of FIG. 4 and channels air flow gently and more evenly to the membranes, while the device 7f is like the device 7a of FIG. 3 and channels most of the air flow towards the lower membranes, providing a greater disruption to the air flow, slowing it down more and allowing the membranes to perform more filtering.

FIGS. 9–36 show various embodiments of the device. As shown in FIG. 9, a device 7g has an air-deflecting head 19 which includes a ridged surface 20, fixed to a stem 22. The stem or support arm 22 has an adhesive for adhering to the septum and includes a lower portion 22a for extending out of the nose to adhere to the bottom of the septum or be wrapped around the septum. Suitable bio-adhesives are well known. Preferably, the stem 22 would be formed as an adhesive tape to which head 19 is attached, and also preferably the stem would be clear for aesthetic reasons. The stem may even have perforations.

The device 7h of FIG. 10 has a stem 23 with an end portion 23a constructed similar to the stem 22 and end portion 22a. Head portion 19a is curved and also has numerous hair-like protrusions 20a.

In FIG. 11, device 7i has a head 19b which also is curved and has numerous pits or protrusions 20b.

The device of FIG. 12 labeled 7j is formed by a body 24 having an adhesive layer for directly adhering to the interior of the septum and has a varying thickness along with a slight convex curve in contrast to the devices of FIGS. 9–11 which have a concave curve with respect to inspired air.

Devices 7k, 7l and 7m of FIGS. 13, 14 and 15, respectively, have rectangular heads 19c, 19d and 19e, respectively. Devices 7k and 7l have adhesive stems 23 while device 7m has an adhesive surface on head 25. Devices 7l and 7m have plain faces while device 7k has a ridged or louvered face 20c.

In FIG. 16, device 7n has an adhesive layer on one side and is substantially elongate. The adhesive layer is integral with the deflection element's body 24. End 24a is for attachment to the septum at the exterior of the nose and may wrap around the septum. The devices 7p, 7q, 7r, 7s, 7t, 7u, 7v of FIGS. 17–23, respectively, have an adhesive layer 24p–24x, respectively, on one face of the device and the opposite face is for deflecting air.

FIG. 17 shows a straight face and an elongate strip. FIG. 18 shows a convex face, although it could be made concave such as shown in FIG. 19. FIG. 20 shows a double-curved device. The device of FIG. 21 shows a V-shaped opening for substantially hindering and slowing air flow, and directing it to the nasal hair region. FIGS. 22 and 23 show different thicknesses of an elongate strip and different lengths in relation to that of FIG. 17. FIG. 24 shows a substantially rectangular device while FIG. 25 shows a substantially oval device.

Figure 27:
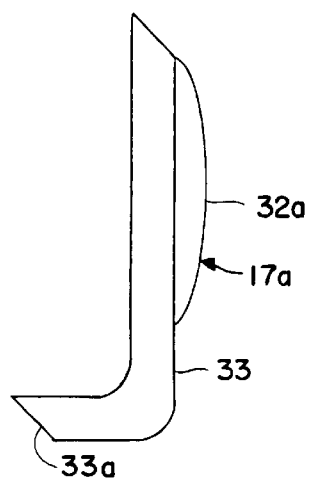
Figure 28:
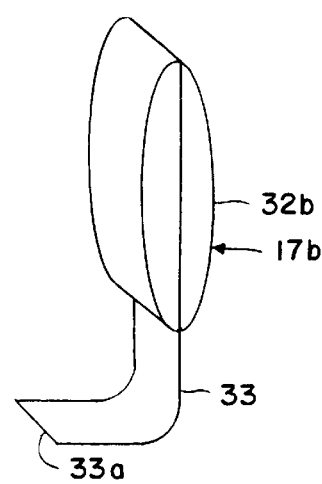

FIGS. 26–29 show use of porous, open-cell or foam-like deflection elements. Device 17 of FIG. 26 has a substantially flexible substrate 33 with a porous material 32 wrapped around it and forming a narrow oval or elliptical shape. Substrate 33 has an end 33a and has an adhesive layer as in previous embodiments for attachment to the septum. FIG. 27 shows a device 17a with a porous material 32a and a semi-elliptical shape and located on one side only of the stem or substrate 33. FIG. 28 shows a device 17b having porous material 32b on each side of the flexible substrate 33 and having an oval or elliptical shape, but each being distinct rather than wrapping around the top of the substrate 33. FIG. 29 shows a substantially oval or elliptical device 17c with a porous material 32c as an outer layer of the oval-shaped head, with three (3) chambers 35, 36 and 37 formed in a material 38 disposed within foam 32c. These chambers may include medicines disposed therein, magnetic devices, perfumes or other olfactory substances, lubricants (e.g., to simulate mucous), and other substances may be disposed in and thus dispensed by the device.

Figure 30:
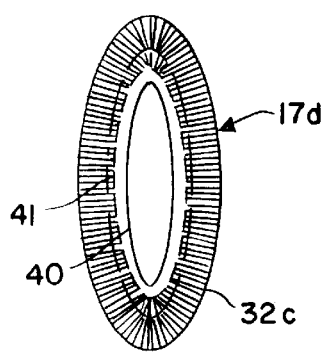
Figure 31:
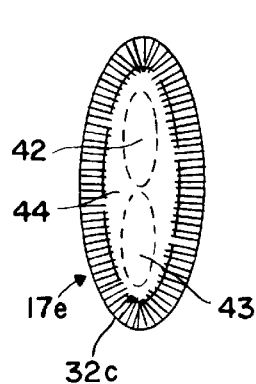

The devices 17d, 17e of FIGS. 30 and 31, respectively, have foam outer layers 32c having chambers formed therein. In FIG. 30, substance 40 is disposed within a chamber 41 with openings that allow the substance to pass to the foam layer 32c by capillary action, pressure or the like. The outer foam layer 32c may be soaked with or include a catalyst to activate the substance 40 or to enhance its distribution. FIG. 31 shows two chambers with substances 42 and 43 which may be the same or different. These two chambers are disposed within a larger chamber 44 and all of the chambers have pores to allow substances to migrate out by pressure or capillary action or the like to be absorbed and dispensed by the foam layer 32c. As in previous embodiments, one of the substances in a chamber may be a catalyst for another substance.

These devices 17d, 17e may be mounted on a substrate as the devices of FIGS. 26–29, or may be directly adhered to the walls of the nasal cavity.

Figure 32:
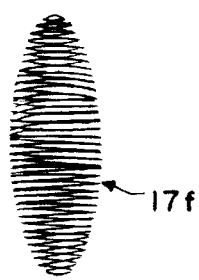
Figure 33:
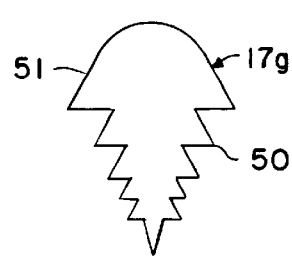
Figure 34:
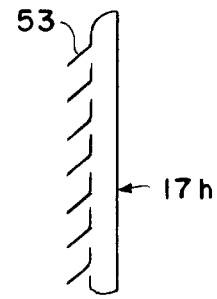

FIG. 32 shows a mesh or textured device 17f having an oval shape. FIG. 33 shows a device 17g with many jagged members or edges 50 to interrupt and thus slow and disperse air inspiration if the device is positioned so that these surfaces 50 are pointed toward the nostril, or expiration if pointed away from the nostril. The device also has a smooth surface 51 to enable smoother air flow for expiration if pointed away from (inward with respect to) the nostril, or smooth inspiration if pointed towards the nostril. The device of FIG. 34, device 17h, has a plurality of louvers 53 which are positioned so as to capture, slow and disperse air flow in one direction yet favor smoother air flow in the other direction. As with the device of FIG. 33, it may be oriented so as to enhance inspiration and slow expiration or to enhance expiration and slow inspiration. The louvers may be adjustable, fixed or respond to air flow.

Figure 35:
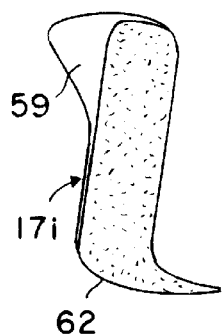
Figure 36:
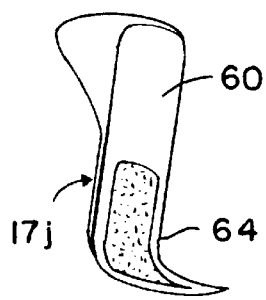

The devices 17i and 17j of FIGS. 35 and 36 have heads 59, 60, respectively, and have adhesive layers or substrates attached to them. In FIG. 35, the adhesive layer or substrate 62 covers an entire surface of the head while the adhesive substrate 64 of FIG. 36 covers only part of the device.

Figure 37:
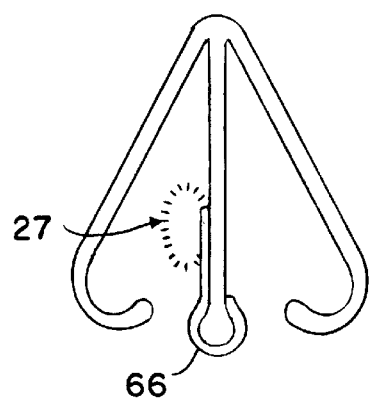
FIGS. 37 and 38 are views similar to FIG. 2 showing alternate embodiments for attaching a nasal device in accordance with the invention to a septum of the nose, FIG. 37 showing a device with a stem which wraps around the septum, and FIG. 38 showing a device with a stem which wraps only partially around the septum.
Figure 38:
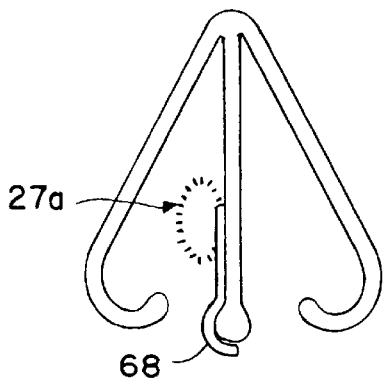
Figure 39:
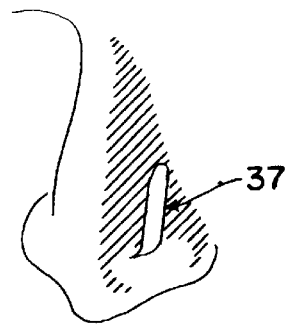
FIGS. 39–42 are schematic views of a nose showing the left nasal cavity with a device in accordance with the invention disposed therein, and various ways to attach the device, FIG. 39 showing a device with a substantially straight profile and an adhesive layer on one side thereof, FIG. 40 showing a device with a bend and having an adhesive strip on one side, FIG. 41 showing a device of an oval shape and having an adhesive layer on one side thereof, and FIG. 42 showing a device with an oval shape and a stem having an adhesive layer on one side thereof.
Figure 40:
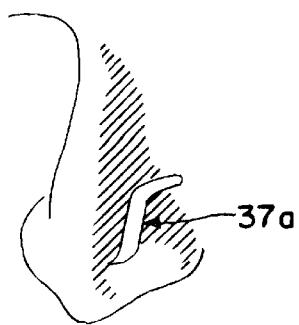
Figure 41:
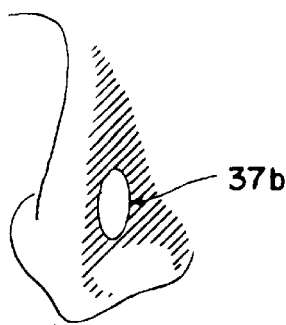
Figure 42:
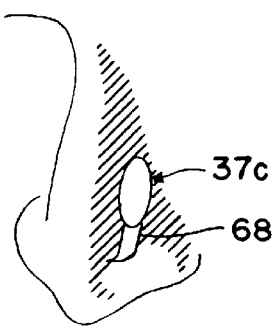

FIGS. 37 and 38 show devices 27 and 27a having adhesive tape or stems 66, 68, respectively, the stem 66 extending around the septum while the stem 68 only goes part way around the septum.

FIGS. 39–42 show devices 37, 37a, 37b and 37c, respectively. Devices 37 and 37a have adhesive layers or tape along one side thereof, device 37b has an adhesive layer on one side thereof and device 37c has an adhesive stem 68.

As noted above, the device and process of the invention enables selective enhancement of the natural functions of the nose including capturing of contaminants in the mucous membrane hair-like material and mucous, directing air through the nasal hairs to filter it, slowing air flow through the nose for better filtering or warming, or selectively affecting air flow upon inspiration and expiration. In addition, air flow may be controlled in a different manner in each nostril. The device may be held in place by an adhesive layer which directly adheres it to the interior of the nose, preferably where the septum would be, or has adhesive tape or an adhesive stem attached to it for adhering to the nasal wall and septum. The device may be of a solid or rigid material, a flexible material, a foam-like material and may have cavities within it for dispensing substances. The device may be constructed of natural materials, polymers or processed natural materials and/or combinations thereof, and may be open-celled, close-celled, geometrically structured, irregularly structured, non-periodic or organic cell formations, fibers, and/or gelatinous in composition. The device may be physically stable, or may include or be soluble or dissolvable or degradable in response to conditions including chemical, air, moisture, temperature, light, electromagnetic radiation, environmental, pressure or air flow, or other conditions to dispense substances or to change its air flow control characteristics.

Preferably, the materials are transparent, or at least translucent or semi-transparent or of a color simulating typical flesh tones particularly typical flesh tones and colors present within nasal passages.

Particularly with the strip-like devices, but also for other device configurations, the use of materials which have some flexibility but may be bent and retain a specific shape are desirable in some embodiments to achieve and adjust desired air flow. It should be noted that the slowing of air flow may enable the nose further to warm or cool incoming air as the mucous membranes are typically more effective at normal body temperatures. The air flow control can thus affect temperature by increasing or decreasing the duration that air flow is within the nose or by increasing or decreasing the area of contact with the body surfaces, and may to some extent affect temperature by friction, compression, cavity volume, moisture, chemical content or other means.

The substances used within the device may have an effect electrically, chemically or on humidity, or may have medicinal effect, such as antiviral, antibacterial, antiseptic, antiallergic, anti-inflammatory, antihistamine properties, as well as lotions, soothing agents, moisturizers, absorbents and/or aromatic substances.

The device and process according to the invention thus controls, manages and conditions inspired and expired air flow and circulation within, around and proximate to the human nasal cavity to influence natural processes, operations or conditions and/or perform supplemental, complementary and/or independent therapeutic processes influencing physiological, physical and/or environmental conditions. The device controls air flow by affecting the direction, duration of contact, route of passage, circulation patterns, pressure, rate, volume, or relative volume reaching various areas of the nasal cavity and adjacent areas such as the sinuses, pharynx, esophagus, oral cavity, bronchial tubes, circulatory and digestive systems to influence natural processes. For example, in some embodiments, air flow is directed to upper regions of the nose while others direct more air flow towards lower regions, which will affect the distribution of air flow to the sinuses versus the pharynx and this relation may be selected by the shape, size, position and construction of the device.

While the present invention has been described with regards to particular embodiments, it is recognized that additional variations of the present invention may be devised without departing from the inventive concept.

What is claimed is:

1. A nasal air flow control device comprising:
an air flow control element for directing air flow in a desired direction or directions when disposed in the nasal cavity, wherein the air flow control element comprises means for deflecting air flow toward at least one of the nasal hair, mucous membranes or a selected nasal passage; and
means for attaching the air flow control element such that the control element is inside the nasal opening, wherein the means for attaching comprises means for adhesively adhering the control element to a portion of the nose.

2. The air flow control device of claim 1 wherein the means for adhering comprises an adhesive layer on the air flow control element.

3. The device of claim 1 wherein the means for adhering comprises an adhesive strip.

4. The device of claim 3 wherein the adhesive strip is for attaching to a septum of the nose.

5. The device of claim 1 further comprising means for holding a substance and dispensing the same when the device is disposed within a nasal cavity.

6. The device of claim 5 wherein the means for holding comprises at least one chamber formed within the flow control element.

7. The device of claim 5 wherein the means for holding comprises an open cell material.

8. The device of claim 5 wherein the substance is at least one of a medicine, olfactory substance, a moisturizer and an electromagnetic element.

9. The device of claim 5 wherein the substance is dispensed by at least one of capillary action, pressure, air flow, or liquid flow.

10. The device of claim 5 wherein the air flow control element deflects the air flow to change the speed of air inspiration or air expiration.

11. The device of claim 1 wherein the air flow control element comprises one of various shapes selected from the group of substantially oval, elliptical, strip-like, curved, rectangular, and multiple curves.

12. The device of claim 1 wherein the air flow control element has a textured surface.

13. The device of claim 12 wherein the textured surface comprises at least one of ridges, bends, double-sided ridges, protrusions, hair-like protrusions and a mesh.

14. The device of claim 1 wherein the air flow control element has a texture for deflecting air in a desired manner in response to air inspiration, and the texture also being for deflecting air in another desired manner in response to expiration.

15. The device of claim 1 wherein the air flow control element has louvers for selectively controlling air flow in response to inspiration and expiration to provide different air flow rates and deflections for inspiration and expiration.

16. A nasal air flow device comprising:
an air flow control element for directing air flow in a desired direction or directions when disposed in a nasal cavity, wherein the air flow control element comprises a member for deflecting air flow with the member toward at least one of the nasal hair, mucosa, or a selected nasal passage; and
means for adhesively attaching the air flow control element for positioning within the nasal opening such that the member deflects the air, wherein the member has a cross-sectional area and the nasal cavity where the device is disposed has an opening area, the cross-sectional area being substantially less than the opening area and the cross-sectional area and opening area being taken in a plane substantially normal to an axial direction of the nasal cavity.

17. The device of claim 16 wherein the member has a textured surface.

18. The device of claim 16 wherein the means for attaching comprises means for adhesively attaching the air flow control element inside the nasal opening.

19. The device of claim 16 wherein the means for deflecting further comprises at least one of means for holding a substance and dispensing the same when the device is disposed within the nasal cavity, means for conditioning the air, and means for filtering the air.

20. A method for controlling air flow upon inspiration or expiration from a nasal cavity, the method comprising the steps of:

adhesively holding and positioning an air flow control element having a member within a nasal cavity; and deflecting air by means of the member upon inspiration to enhance air flow in the direction of at least one of nasal hair, nasal mucous membranes, and selected nasal passages, wherein the device is positioned such that substantially less than the entire cross-sectional area of the nasal opening is blocked by the device.

* * * * *